United States Patent [19]

Pruss

[11] Patent Number: 5,731,354
[45] Date of Patent: Mar. 24, 1998

[54] TREATMENT FOR THE INHIBITION OF NEURO-DEGENERATIVE DISEASE STATES

[75] Inventor: Thaddeus P. Pruss, Madison, Wis.

[73] Assignee: Clarion Pharmaceuticals Inc., Madison, Wis.

[21] Appl. No.: 643,567

[22] Filed: May 6, 1996

[51] Int. Cl.$^6$ .................................................. A61K 31/08
[52] U.S. Cl. ............................................................ 514/723
[58] Field of Search ............................................. 514/723

[56] References Cited

PUBLICATIONS

Chemical Abstracts AN 1988:545322, Zoeller et al., Jan. 1988.
Das et al. (1992); "Dietary Ether Lipid Incorporation Into Tissue Plasmalogens of Humans and Rodents," *LIPIDS*, 27(6):401–405.
Hermetter and Paltauf (1995); in "Phospholipids: Characterization, Metabolism, and Novel Biological Applications," Cevc, G., Palauf, F., Eds.; pp. 260–273: AOCS Press, Champaign, Illinois.
Horrocks (1972); in "Ether Lipids: Chemistry and Biology," Snyder, F. Ed., pp. 177–272.
Nunez and Clarke (1994); "The Bcl–2 Family of Proteins: Regulators of Cell Death and Survival," *Trends in Cell Biology*, 4:399–403.
Paltauf, F. (1994); "Ether lipids in biomembranes," *Chemistry and Physics of Lipids*, 74:101–139.
Reder, A. T.; Thapar, M.; Sapugay, A.M.; Jensen, M.A. (1994); *Journal of Neuroimmunology*, 54:117–127.
Reiter (1995); "Oxidative Processes and Antioxidative Defense Mechanisms in the Aging Brain," *FASEB*, 9:526–533.
Selmaj, K.; Papierz, W.; Glabinski, A.; Kohno, T. (1995); *Journal of Neuroimmunology*, 56:135–141.
Wanders et al. (1986); *J. Inher. Metab. Dis.*, 9:335–342.
Zoeller et al., A Possible Role for Plasmalogens in Protecting Animal Cells against Photsensitized Killing (1988), *The Journal of Biological Chemistry*, vol. 263, No. 23, pp. 11590–11596.

*Primary Examiner*—Keith MacMillan
*Attorney, Agent, or Firm*—DeWitt Ross & Stevens S.C.; Salvatore R. Conte, Esq.

[57] ABSTRACT

A method of inhibiting degeneration of neural cells comprising treating the cells with an effective degeneration-inhibiting amount of one or more compounds of Formula I:

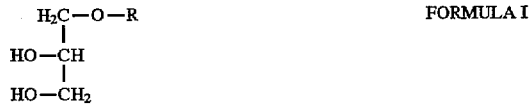

FORMULA I wherein R is a $C_{12}$ to $C_{22}$ linear or branched alkyl group, or pharmaceutically-acceptable salts thereof is disclosed.

12 Claims, No Drawings

TREATMENT FOR THE INHIBITION OF NEURO-DEGENERATIVE DISEASE STATES

FIELD OF THE INVENTION

The present invention is directed to the inhibition of nerve cell degeneration leading to cell death by treating the nerve cell with a metabolic precursor of one or more phospholipid compounds.

BIBLIOGRAPHY

Complete bibliographic citations for the references cited below are included in the "Bibliography" section immediately preceding the claims. All of the references cited below are incorporated by reference herein in their entirety.

DESCRIPTION OF THE PRIOR ART

Glycerophospholipids and related glycerol-derived lipid analogs are ubiquitous compounds which are major constituents in mammalian cellular membranes. As a class of compounds, these lipids share the common feature of a 3-carbon glycerol backbone. A wide range of physiologically important compounds, such as phosphatidic acid analogs, fatty acid and aldehyde glycerols, ether glycerol phospholipids, plasmalogens, and the like, are defined by the chemical side chains attached to the glycerol backbone. The side chains are linked to the glycerol backbone via several different types of bonds, including ester linkages, ether linkages, phosphoether linkages, and alk-1'-enylether linkages.

Ether glycerophospholipids bearing an alk- 1'-enyletherlinked substituent are given the trivial class name plasmalogens. Plasmalogens are generally thought to play an important, albeit undefined, role in cellular growth, maintenance, and apoptosis. For instance, it is thought that plasmalogens may function as antioxidants in vivo. The biological effect of any such antioxidative functionality of plasmalogens, however, remains uncertain. Reiter (1995) notes that aging in general, and aging of the central nervous system in particular, may relate to damage inflicted by free radical oxygen species. Reiter further notes that this hypothesis is supported by considerable experimental data. Reiter also reflects, however, that while age-related neurodegenerative conditions such as Alzheimer's disease, multi-infarct dementia, and amyotrophic lateral sclerosis (ALS) have been extensively studied in terms of their causative factors, there is no definitive etiology for any of the above-noted conditions. Moreover, the uncertainty of the role played by reactive oxygen intermediates, if any, in programmed cell death is summed up by Nunez and Clarke (1994), who note that "it is unclear whether reactive intermediates are required for apoptosis."

For an excellent review of the present scientific knowledge regarding ether phospholipids in biomembranes, see Paltauf (1994).

Particularly helpful in understanding the general field to which the present invention pertains is Paltauf's discussion of ether lipid biosynthesis and metabolism in mammalian cells. An interesting feature of the biosynthetic pathway is that two of the enzymes involved in the formation of an alkyl ether bond to the glycerol backbone, namely dihydroxyacetone phosphate acyltransferase (DHAP-AT) and alkyldihydroxyacetone phosphate synthase (alk-DHAP synthase) are located solely in the peroxisomes. Consequently, the biosynthetic pathway leading from dihydroxyacetone phosphate (DHAP) to glycerophospholipids is divided between cytosolic reactions (at both the initial and final stages of synthesis) and peroxisome-located reactions. A significant consequence of this cytosol/peroxisome division is that disorders which affect the functioning of the peroxisomes, such as cerebro-hepato-renal Zellweger's syndrome, may have a notable effect on the biosynthesis of a variety of phospholipid compounds.

The metabolic pathway leading from DHAP to various glycerophospholipids, as described by Paltauf (1994) is summarized below.

DHAP from the cytoplasm is first imported into the peroxisome, where it then reacts with acyl CoA to yield a 1-acyl-3-hydroxyacetone phosphate. This first reaction is catalyzed by DHAP-AT. Enzymatic reaction with a primary alcohol (catalyzed by alkyl-DHAP-synthase) then yields the 1-alkylether-3-hydroxyacetone phosphate analog. Further reaction with NADPH causes reduction of the 2-position carbonyl into an alcohol. At this point, the 1-alkylether-2-hydroxyglycerol-3-phosphate intermediate is transported out of the peroxisome for further biosynthetic reactions in the cytoplasm or endoplasmic reticulum (ER). The biosynthetic reactions which occur solely within the peroxisomes are summarized as follows:

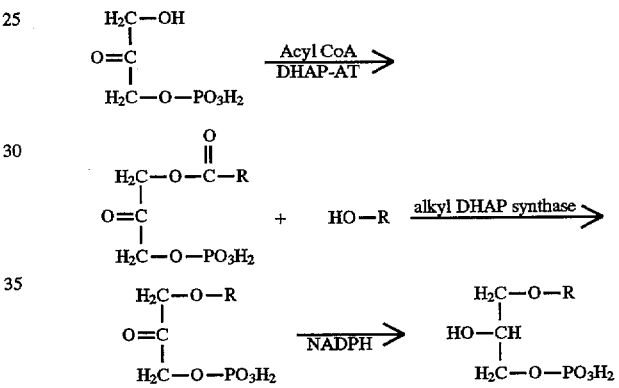

Outside of the peroxisome, plasmalogens are formed by the step-wise acylation of the 2-position carbonyl, amine functionalization of the 3-position orthophosphate (as with choline or ethanolamine), followed by enzymatic dehydrogenation of the 1-position alkylether side chain.

Paltauf notes that in peroxisomal disorders such as Zellweger's syndrome and rhizomelic chondrodysplasia punctata (RHCP), the impediment to the peroxisomal enzymatic reactions may be circumvented by providing to the ether lipid-deficient cells a suitable precursor which can be used for plasmalogen synthesis in the ER. For instance, Paltauf notes that the fibroblast from healthy donors contain approximately 15% ethanolamine plasmalogen. However, supplying exogenous alkylglycerol to these normal cells has no effect on the plasmalogen content of the cells. In contrast, the reduced plasmalogen levels found in cultured fibroblasts of Zellweger's or RHCP patients can be elevated to almost normal levels if the cells are cultured in the presence of an alkylglycerol. (See also, Hermetter and Paltauf (1995).)

It must be noted, however, that very little is known about the ether lipid content of other tissues in patients suffering from peroxisomal disorders. See, for instance, Das et al. (1992). Das et al. note that chronic feeding of 1-O-octadecyl-sn-glycerol (batyl alcohol) to human patients suffering from peroxisomal disorders which result in a low tissue content of ether glycerolipids, results in increased plasmalogen content within their red blood cells (erythrocytes). Das et al. were interested in whether the oral administration of ether lipids to patients with peroxisomal disorders might increase the concentration of tissue ether lipids. Das et al. convincingly show that chronic oral administration of batyl alcohol to patients suffering from certain peroxisome dysfunction disorders results in a significant increase in red blood cell ethanolamine plasmalogen concentration. This leads Das et al. to conclude that the administration of oral ether lipids represents a "potential" treatment for patients with peroxisomal disorders.

This conclusion, however, must be treated with caution in that while Das et al. noted that the infant subjects described therein showed improved nutritional status, liver function, retinal pigmentation, and replenishment of deficient erythrocyte ethanolamine plasmalogen level by the feeding of ether lipids, Das et al. also conclude that it is not possible to separate these changes from the natural history of the untreated disease. For instance, Wanders et al. (1986) have documented that plasmalogen levels in Zellweger's syndrome patients increase naturally as a function of age. It is hypothesized that this may be due to the intake of natural alkyl glycerols present in food. Horrocks (1972) estimates that the average adult consumes from 10–100milligrams of batyl alcohol per day.

Das et al. also investigated the extent of incorporation of dietary ether lipids into tissue lipids by administering different precursors of the ether lipids, such as heptadecanoic acid, heptadecanol, 1O-heptadecyl-sn-glycerol, and 3-O-heptadecyl-sn-glycerol, to young rats. Das et al.'s data indicate that natural glycerols are incorporated more readily than unnatural optical isomers. While the precursors were incorporated into various plasmalogens, the total plasmalogen content of the tissues tested did not increase. The relative incorporation rates of the various ether lipid precursors is reported by Das et al. to be as follows: 1-O-heptadecyl-sn-glycerol>heptadecanol>heptadecanoic acid>3-O-heptadecyl-sn-glycerol. This leads Das et al. to conclude that while most exogenous long chain ether lipids are eventually incorporated into alkylglycerol ether lipids, the subsequent conversion of the alkylglycerol ether lipids into plasmalogens occurs only in those lipids containing a 1-alkyl side chain of between $C_{15}$ and $C_{19}$ which is fully saturated or mono-unsaturated.

It is against this background of uncertain biological functionality, that a number of patents describe the use of glycerol derivatives in the treatment of various disease states. For instance, Horrmann, U.S. Pat. Nos. 4,505,933 and 4,687,783, describes a treatment for multiple sclerosis and "shaking paralysis," respectively, by orally administering a linear, unsaturated fatty aldehyde or acid derivative to a patient. Specifically, the two Horrmann patents describe the treatment of multiple sclerosis or "shaking paralysis" by orally administrating a mixture of 6-n-dodecenoic aldehyde, 8-n-hexadecenoic aldehyde, and 8-n-hexadecenoic acid, followed by further oral administration of 6,12-n-octadecadienoic aldehyde, 8,16-n-tetracosadienoic-2-hydroxy aldehyde, and 8,16-n-tetracosadienoic-2-hydroxy acid.

Chalmers et al., U.S. Pat. No. 3,294,639, describe the treatment of inflammatory diseases such as rheumatoid arthritis by administering chimyl, selachyl, or batyl alcohol to a patient. A treatment for asthma utilizing the same compounds is described by Brohult et al., U.S. Pat. No. 5,173,511. These compounds are 1-position monoethers of glycerol: chimyl alcohol is the hexadecyl monoether, selachyl alcohol the octadecenyl (i.e., oleyl) monoether, and batyl alcohol the octadecyl monoether. Synthesis of these compounds is well known in the art (see, for instance, Takaishi et al., U.S. Pat. No. 4,465,869 and UK Patent 1,029,610).

SUMMARY OF THE INVENTION

The present invention is drawn to a method of inhibiting the degeneration of neural cells. The method comprises treating the cells with an effective neural cell degeneration-inhibiting amount of one or more compounds of Formula I:

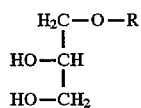

FORMULA I wherein R is a $C_{12}$ to $C_{22}$ linear or branched alkyl group, and pharmaceutically-acceptable salts thereof.

A principal aim and object of the present invention is to provide a treatment for the inhibition of neuro-degenerative disease states in humans which utilizes one or more metabolic precursors or analogs of naturally-occurring lipid compounds.

A further aim of the invention is to provide a method to inhibit the degeneration of neural cells leading to premature apoptosis and cell death.

A distinct advantage of the present invention is that it provides an effective inhibitory treatment for several devastating neuro-degenerative disease states in humans, including stroke, Alzheimer's disease, multiple sclerosis (MS), and amyotrophic lateral sclerosis (ALS). Over sometimes great spans of time, these disease states leave patients as empty shells of their former selves. Alzheimer's disease effectively robs its victims of their memories and cognitive functions, while maladies such as MS and ALS result in a slow, inexorable wasting away of the body. Stroke, while acute in its initial onset, often results in long-lasting and progressive physical and cognitive impairments.

Because these disease states are chronic and normally not immediately fatal to the patient, they also inflict ongoing emotional as well financial hardships on the families of the afflicted. The present invention ameliorates these hardships by inhibiting the further progression of the disease. Physiologically, the active ingredients described herein have been shown to inhibit the degeneration of nerve cells which leads to cell death. By inhibiting the progression of nerve cell degeneration, and thereby inhibiting further nerve cell death, the present method of treatment and pharmaceutical composition inhibits the worsening of the physical and cognitive symptoms due to neuro-degenerative diseases.

DETAILED DESCRIPTION OF THE INVENTION

It has been discovered that treating neural cells with one or more of the compounds of Formula I, above, inhibits degeneration of the cells leading to cell death. Furthermore, it has been found that pharmaceutical compositions containing these compounds are effective to inhibit neuro-degenerative disease states in human beings.

As used herein, the term "neuro-degenerative disease states" refers to those disease states in mammals, including humans, in which symptoms are due to degeneration or inactivation nerve cells (i.e., neurons of any type and bodily location, including the brain, the central nervous system, or the periphery). This degeneration is thought to be caused by damage inflicted by oxygen-derived free radicals. Explicitly included within the term "neuro-degenerative disease states" are stroke, Alzheimer's disease, multiple sclerosis (MS), and amyotrophic lateral sclerosis (ALS). This list is exemplary, not exclusive. The method described herein can be used to treat other neuro-degenerative diseases in addition to those disorders listed.

Neuro-degenerative diseases are generally characterized by the formation of patches of sclerosis or "plaques" at the effected site. The various symptoms suffered by any given patient depends largely upon the location of the lesions. For instance, in the case of MS (disseminated, focal, or insular), plaques are found in the brain and spinal cord. Symptoms include paralysis, tremor, rhythmic oscillation of the eyeballs (nystagmus), and disturbances in speech. In the case of ALS, plaques form upon the lateral columns and anterior horns of the spinal cord. Here, progressive muscular atrophy is the predominant symptom. In Alzheimer's disease, senile plaques appear in the brain. Progressive memory loss followed by severe impairment of cognitive abilities is the most predominant symptom.

While expressly disavowing any limitation to a given mode of action, it is thought that the inhibitory action of the present invention is accomplished by increasing the availability of metabolic precursors or suitable substrates for the biosynthesis of free radical-scavenging molecules, most notably plasmalogens. By providing neural cells with either suitable substrates for plasmalogen synthesis by normal routes, or by inducing alternative pathways for plasmalogen synthesis, it is believed that the neural cells are thereby enabled to circumvent further deterioration caused by neuro-degenerative conditions. This protective effect results from an increase in the free radical scavenging ability of the neural cells.

Consequently, the present invention provides a method of inhibiting free radical-mediated neural cell degeneration in a host mammal afflicted with a neuro-degenerative disorder which comprises administering to the mammal an effective free radical degeneration-inhibiting mount of one or more compounds of Formula I or pharmaceutically-acceptable salts thereof.

From among the compounds of Formula I, the preferred compounds for use in the present invention are the compounds wherein R is a $C_{16}$ to $C_{18}$ linear or branched alkyl group. Chimyl and batyl alcohol are most preferred. The preferred pharmaceutically-acceptable salts of the compounds of Formula I are mono or di-substituted basic salts such as sodium, potassium, and calcium salts.

I. Stroke

The compounds of Formula I and their pharmaceutically-acceptable salts possess anti-degenerative activity in neural cells and can be used in the treatment of stroke (i.e., apoplexy). After the initial onset of stroke, progressive and further injury to the neurons deprived of oxygen can occur during the intense respiratory burst which occurs as the acute blockage is cleared (normally with anti-coagulant treatment such as heparin or coumarin). This respiratory burst generates oxygen-derived free radical species which cause further damage to the already weakened neurons.

The compounds of Formula I preferably are administered as soon as possible after the onset of stroke to prevent ischemic or reperfusion injury as the thrombosis or embolism subsides and normal circulation is restored to the effected area. Preferably, the treatment is begun well within 24 hours of onset of the stroke.

It is preferred that an initial loading dose of a compound of Formula I be administered to the patient by intravenous drip. Once the initial loading dose has been administered, and the patient's condition stabilized, the method can be practiced using an orally administered formulation of the subject compounds. By preventing ischemic or reperfusion injury following stroke, the present method can inhibit chronic and progressive cognitive and physical impairments caused by stroke.

The ability of the subject compounds to increase viability of neural cells after exposure to oxygen-derived radicals is illustrated in Example I. In this Example, various neural cells are exposed to UV radiation, which generates harmful free radicals. Treating the neural cells with compounds of Formula I and their pharmaceutically-acceptable salts increases the viability of neural cells after exposure to UV light.

The invention thus provides a method of treating stroke in a host mammal afflicted with stroke comprising administering to the mammal one or more compounds of Formula I or pharmaceutically-acceptable salts thereof in an amount effective to inhibit stroke-related neural degeneration.

II. Alzheimer's Disease

As noted above, Alzheimer's disease is characterized by the presence of senile plaques in the brain. While the etiology of Alzheimer's disease is unknown, the plaques are thought to be due to free radical damage which leads to cell death and the formation of the plaques. As illustrated in Example 1, below, the subject compounds increase the viability of brain tumor cells exposed to UV light with the concomitant generation of oxygen-derived free radical species.

Consequently, by treating brain cells with compounds of the present invention, via administration of the compounds to an Alzheimer's patient in need thereof, free-radical damage to the patient's brain cells can be inhibited.

The subject invention thus provides a method of treating Alzheimer's disease in a host mammal afflicted with Alzheimer's disease which comprises administering to the mammal one or more compounds of Formula I or pharmaceutically-acceptable salts thereof in an amount effective to inhibit progression of the Alzheimer's disease.

III. Multiple Sclerosis

Multiple sclerosis (MS) is another neuro-degenerative disorder wherein free radicals inflict cellular damage to neurons. It is also of unknown etiology.

Experimental Allergic Encephalomyelitis (EAE), an animal model for multiple sclerosis, is mediated by immune mechanisms in which macrophage activation and the generation of oxygen-derived free radicals play a major role. In mice, induced EAE causes reversible paralysis which mimics multiple sclerosis. Left untreated, induced EAE normally resolves spontaneously approximately 8 to 10 days after the onset of symptoms.

Example 2, below, demonstrates the preventive and ameliorative effects exhibited by the subject compounds when administered to EAE-induced mice. The inhibitory effect of the subject compounds and their pharmaceutically-acceptable salts on the onset and progression of EAE in mice is predictive of its effect in human subjects.

The invention thus provides a method of treating multiple sclerosis in a host mammal afflicted with multiple sclerosis comprising administering to the mammal one or more compounds of Formula I or pharmaceutically-acceptable salts thereof in an mount effective to inhibit progression of the multiple sclerosis.

IV. Amyotrophic Lateral Sclerosis

Amyotrophic lateral sclerosis (ALS) is related to multiple sclerosis in that its symptoms are caused by sclerotic degeneration of the spinal cord leading to progressive muscular atrophy. Its etiology is also unknown.

As predicted by Example 2, below, the subject compounds inhibit degeneration of neural cells in EAE-induced mice. This induced disease state involves cellular damage to neural cells via free radical mechanisms. In conjunction with Example 1, the compounds of the present invention are inhibitors of free radical-induced cellular damage. Consequently, the compounds of Formula I and their pharmaceutically-acceptable salts are useful for the treatment and inhibition of the progression of ALS.

The invention thus provides a method of treating amyotrophic lateral sclerosis in a host mammal afflicted with amyotrophic lateral sclerosis which comprises administering to the mammal one or more compounds of Formula I or pharmaceutically-acceptable salts thereof in an amount effective to inhibit progression of the amyotrophic lateral sclerosis.

V. Routes of Administration and Dosage

In mammalian subjects, the compounds of Formula I can be administered orally, parenterally (including subcutaneous, intradermal, intramuscular and intravenous injection), rectally, and topically (including dermal, buccal, and sublingual administration) in combination with an inert liquid or solid pharmaceutically-acceptable carrier which is suitable for the method of administration chosen. Such pharmaceutical carriers are well known in the art.

In in vitro applications, such as in the study of mutant cell types or other cellular investigations, the pharmaceutical compositions of the present invention are preferably administered to the cells by adding a pre-defined amount of a compound of Formula I, diluted in a suitable diluent, to the cell culture medium. As used herein, the terms "administering" or "administration" are synonymous with "treating" or "treatment." In essence, administering to cells in vitro one or more of the compounds of Formula I entails contacting the cells with the compounds or salts of the compounds.

The in vivo dosage in humans and other mammals depends largely upon the affliction being treated, the time since onset of the condition, the progression of the disease, and the age and general health of the patient being treated. Determining the optimum dosage for any given patient is essentially an empirical and ongoing process. Inhibition of neural degeneration in infants and children who are diagnosed early in the progression of the neuro-degenerative condition may optimally require a more (or less) aggressive treatment than older patients in more terminal stages of a neuro-degenerative condition. Of primary importance in optimizing the most effective dosage is that each patient be carefully monitored throughout the course treatment to follow the progression, if any, of the condition.

A suitable effective dose for most conditions ranges from about 1 mg/kg body weight to about 2 g/kg body weight per day, and is preferably in the range of from about 100 to about 500 mg/kg body weight per day (calculated as the non-salt form). The total daily dose may be given as a single dose, multiple doses, e.g., two to six times per day, or by intravenous infusion for a selected duration. Dosages above or below the above-cited ranges are within the scope of the invention and such dosages may be administered to individual patients if the circumstances so dictate.

For example, in a 75 kg mammal, a typical daily dosage might fall within the range of from about 100 mg to about 100 g per day. If discrete multiple doses are indicated, treatment might typically comprise 4 equal fractional doses given at 8 hour intervals to supply the total daily dosage.

VI. The Active Ingredients

The active ingredients used in the above-described method are alkyl monoethers of glycerol. The compounds themselves are known and several methods for their preparation are described in the chemical literature. All optical, geometric, and positional isomers of the compounds of Formula I, including racemic mixtures or pure or enriched enantiomeric forms, geometric isomers, and mixtures thereof, are within the scope of this invention.

By the term "pharmaceutically-acceptable salt" is meant any salt conventionally used in the formulation and administration of pharmaceutical preparations. This term encompasses inorganic salts such as nitrates, phosphates, sulfates, and chlorides, as well as mono and di-substituted basic salts of sodium, potassium, calcium, and the like. Organic salts such as malonates, fumarates, succinates, crotonates, and the like are also encompassed by the term "pharmaceutically-acceptable salt." The foregoing list is exemplary, not exclusive. A large number of salts acceptable for pharmaceutical administration are known to those of skill in the art.

EXAMPLES

The following Examples are intended to illustrate and not to limit the scope of the present invention.

Example 1
In Vitro Inhibition of UV-Generated Free Radical Damage in Brain Tumor Cells Brain tumor cell lines designated SF-268, SF-295, SF-539, SNB-19, SNB-75, and U251, available from the National Cancer Institute, Bethesda, Md., are cultured in Dulbecco's modified Eagle Medium (DMEM) containing 10% fetal bovine serum (FBS), 1% non-essential amino acids, 2 mM L-ghutamine, 50 µM 2-mercaptoethanol, 100 U/ml penicillin, and 100 U/ml streptomycin sulfate (referred to herein as DMEM-10). The cells are cultured in standard T-75 or T-150 flasks at 37° C. under a humid, 5% $CO_2$ atmosphere. Sterility of the cultures is strictly maintained. The cells are passaged when approximately 80% confluent using trypsin and EDTA (0.5% w/v trypsin and 0.2% EDTA). Sub-cultures are incubated under identical conditions.

Multiple control cell samples are assembled at a concentration of $1 \times 10^6$ cells per ml in fresh DMEM-10 media. Multiply duplicative test cell samples are assembled in fresh DMEM-10 media which contains a desired concentration of one or more compounds of Formula I.

The control samples and the test samples are then incubated at various fixed periods of time at 37° C. in 5% $CO_2$.

The control samples and the test samples are then exposed for 30 minutes to a 365 nm wavelength UV light source. This UV light exposure generates free radical oxygen species which induce cell death.

At fixed time periods after the UV treatment, cell viability is measured in both the control samples and the test samples by uptake of $^3H$ thymidine, using procedures which are well known in the art.

The results show that treating such cells with one or more compounds of Formula I or its pharmaceutically-acceptable salts confers increased viability to the cells after in vitro exposure to UV radiation.

Example 2
In Vivo Inhibition of Central Nervous System Degeneration in Experimental Allergic Encephalomyelitis in Mice Experimental Allergic Encephalomyelitis (EAE) is an experimental model for multiple sclerosis. EAE is mediated by immune mechanisms in which macrophage activation and the generation of oxygen-derived free radicals play a major role.

Female SJL/J ($H-2^8$) mice (6 to 10 weeks old, available from Jackson Labs) are used for the model. To induce EAE, on Day 0 the mice are intravenously injected with about $1 \times 10^7$ to $1 \times 10^8$ myelin-based protein-sensitized lymph node cells (MBP cells).

The MBP cells themselves are produced in mice which are immunized 10 days beforehand with 0.4 mg of myelin-based protein in complete Freund's adjuvant (CFA). Seven days after immunization of these mice, MBP cells are harvested and cultured for three days in the presence of 50 µg/ml myelin-based protein. (The culture media is RPMI 1640, supplemented with 10% FBS, non-essential amino acids, penicillin, and streptomycin, as described in Example 1 for the DMEM media.) The MBP cells so produced are used to induce EAE in the test mice, as described above.

Myelin-based protein for the test is prepared from guinea pig spinal cords via a known procedure (See, for example, Reder et al. (1994) and Selmaj et al. (1995).)

Onset of the induced EAE occurs within Day 6 to Day 8, and persists until Day 16 to Day 19. The induced EAE disease state then spontaneously resolves.

In a preventive study, fixed dosages of compounds of Formula 1 are administered intravenously in a suitable pharmaceutical carrier to a sub-population of the EAE-induced mice at fixed time intervals beginning at Day 0.

In a treatment study, fixed dosages of compounds of Formula 1 are administered intravenously in a suitable pharmaceutical carrier to another sub-population of the EAE-induced mice at fixed time intervals beginning immediately after the animals show clinical onset of the EAE disease state.

The test and control animals are observed for clinical signs of EAE and graded according to the following criteria:

0=normal

1=limp tail

2=mild to moderate hind limb weakness

3=hind leg paralysis

4=moderate weakness of forelimbs

5=moribund or death

Animals are observed 2 times per day and are weighed every other day.

Moribund animals are sacrificed by cervical separation or $CO_2$, and all animals are sacrificed by Day 18 by $CO_2$. Tissue samples are taken from the sacrificed animals for further histological and cytological studies.

The results from both the preventive and treatment studies described above show that administration of one or more compounds of Formula I or its pharmaceutically-acceptable salts to a mammal afflicted with a neuro-degenerative disease delays the onset of symptoms of the disease and also slows the progression of the disease once its onset has become apparent.

It is understood that the invention is not confined to the embodiments herein illustrated and described, but embraces all such modified forms thereof as come within the scope of the attached claims.

BIBLIOGRAPHY

Das et al. (1992); "Dietary Ether Lipid Incorporation Into Tissue Plasmalogens of Humans and Rodents," *LIPIDS*, 27 (6): 401–405.

Hermetter and Paltauf (1995); in "Phospholipids: Characterization, Metabolism, and Novel Biological Applications," Cevc, G., Palauf, F., Eds.; pp. 260–273: AOCS Press, Champaign, Ill.

Horrocks (1972); in "Ether Lipids: Chemistry and Biology," Snyder, F. Ed., pp. 177–272.

Nunez and Clarke (1994); "The Bcl-2 Family of Proteins: Regulators of Cell Death and Survival," *Trends in Cell Biology*, 4:399–403.

Paltauf, F. (1994); "Ether lipids in biomembranes," *Chemistry and Physics of Lipids*, 74: 101–139.

Reder, A. T.; Thapar, M.; Sapugay, A. M.; Jensen, M. A. (1994); *Journal of Neuroimmunology*, 54:117–127.

Reiter (1995); "Oxidative Processes and Antioxidative Defense Mechanisms in the Aging Brain," *FASEB*, 9:526–533.

Selmaj, K.; Papierz, W.; Glabinski, A.; Kohno, T. (1995); *Journal of Neuroimmunology*, 56:135–141.

Wanders et al. (1986); *J. Inher. Metab. Dis.*, 9:335–342.

What is claimed is:

1. A method of inhibiting free radical-mediated neural cell degeneration in a host mammal afflicted with a neuro-degenerative disorder comprising administering to said mammal an effective free radical degeneration-inhibiting amount of one or more compounds of Formula I:

wherein R is a $C_{12}$ to $C_{22}$ linear or branched alkyl group, or pharmaceutically-acceptable salts thereof.

2. The method of claim 1, wherein an amount of the compound of Formula I is administered to a human patient afflicted with a neuro-degenerative disorder in need thereof which is effective to inhibit degeneration of the neural cells.

3. The method of claim 2, wherein the compound of Formula I is administered parenterally in combination with a pharmaceutically-suitable liquid carrier.

4. The method of claim 2, wherein the compound of Formula I is administered orally in combination with a pharmaceutically-suitable liquid or solid carrier.

5. The method of claim 2, wherein the compound of Formula I is administered to a human stroke, Alzheimer's disease, multiple sclerosis, or amyotrophic lateral sclerosis patient in need thereof in an amount which is effective to inhibit progression of neuro-degeneration due to the stroke, Alzheimer's disease, multiple sclerosis, or amyotrophic lateral sclerosis.

6. The method of claim 5, wherein a compound of Formula I wherein R is selected from the group consisting of $C_{16}$ to $C_{18}$ linear or branched alkyl, pharmaceutically-acceptable salts thereof, and combinations thereof is administered to the human patient.

7. The method of claim 5, wherein a compound of Formula I selected from the group consisting of chimyl alcohol, batyl alcohol, pharmaceutically-acceptable salts thereof, and combinations thereof is administered to the human patient.

8. A method of inhibiting or treating stroke, Alzheimer's disease, multiple sclerosis or amyotrophic lateral sclerosis in a human patient afflicted with same comprising administering to the human patient an effective anti-stroke, anti-Alzheimer's disease, anti-multiple sclerosis or anti-amyotrophic lateral sclerosis amount of one or more compounds of Formula I:

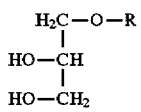 FORMULA I wherein R is a $C_{12}$ to $C_{22}$ linear or branched alkyl group, or pharmaceutically-acceptable salts thereof.

9. The method of claim 8, wherein the compound of Formula I is administered parenterally in combination with a pharmaceutically-suitable liquid carrier.

10. The method of claim 8, wherein the compound of Formula I is administered orally in combination with a pharmaceutically-suitable liquid or solid carrier.

11. The method of claim 8, wherein a compound of Formula I wherein R is selected from the group consisting of $C_{16}$ to $C_{18}$ linear or branched alkyl, pharmaceutically-acceptable salts thereof, and combinations thereof is administered to the human patient.

12. The method of claim 8, wherein a compound of Formula I selected from the group consisting of chimyl alcohol, batyl alcohol, pharmaceutically-acceptable salts thereof, and combinations thereof is administered to the human patient.

* * * * *